(12) United States Patent
Cromwell et al.

(10) Patent No.: US 7,812,956 B2
(45) Date of Patent: *Oct. 12, 2010

(54) TIME DEPENDENT FLUORESCENCE MEASUREMENTS

(75) Inventors: Evan F. Cromwell, Redwood City, CA (US); Johann F. Adam, Palo Alto, CA (US); Andrei Brunfeld, Cupertino, CA (US); Paul B. Comita, Menlo Park, CA (US); Christopher J. Seipert, San Jose, CA (US)

(73) Assignee: Blueshift Biotechnologies, Inc., Sunnyvale, CA (US)

( * ) Notice: Subject to any disclaimer, the term of this patent is extended or adjusted under 35 U.S.C. 154(b) by 86 days.

This patent is subject to a terminal disclaimer.

(21) Appl. No.: 12/072,047

(22) Filed: Feb. 22, 2008

(65) Prior Publication Data

US 2008/0174842 A1    Jul. 24, 2008

Related U.S. Application Data

(63) Continuation of application No. 10/927,748, filed on Aug. 26, 2004, now abandoned.

(60) Provisional application No. 60/497,803, filed on Aug. 26, 2003, provisional application No. 60/497,764, filed on Aug. 26, 2003.

(51) Int. Cl.
| | |
|---|---|
| *G01N 21/55* | (2006.01) |
| *G01N 21/25* | (2006.01) |
| *G01N 21/00* | (2006.01) |
| *G01N 21/64* | (2006.01) |
| *G01J 3/30* | (2006.01) |
| *G01J 1/58* | (2006.01) |
| *G01J 1/10* | (2006.01) |
| *F21V 9/16* | (2006.01) |
| *G21H 3/02* | (2006.01) |
| *H01J 65/06* | (2006.01) |
| *H01J 65/08* | (2006.01) |

(52) U.S. Cl. .................. 356/445; 356/317; 356/318; 356/417; 422/82.05; 422/82.07; 250/458.1

(58) Field of Classification Search .................. None
See application file for complete search history.

(56) References Cited

U.S. PATENT DOCUMENTS 3,013,467 A    12/1961    Minsky (Continued)

FOREIGN PATENT DOCUMENTS

EP    0 440-342 A    8/1991

(Continued)

OTHER PUBLICATIONS

Lakowicz et al., "Anisotrophy-Based Sensing with Reference Fluorophores," Oct. 20, 1998, Analytical Biochemistry 267, 397-405 (1999).

(Continued)

*Primary Examiner*—Tarifur Chowdhury
*Assistant Examiner*—Gordon J Stock, Jr
(74) *Attorney, Agent, or Firm*—Weaver Austin Villeneuve & Sampson LLP

(57) ABSTRACT

Methods and apparatus, including computer program products, implementing and using techniques for collecting optical data pertaining to one or more characteristics of a sample. The apparatus has a light source, one or more illumination optical elements, a scanner, one or more collection optical elements, and a device forming an aperture that limits detection of light from the sample. The illumination optical elements direct a light beam from the light source onto the sample. The scanner scans the light beam across the sample. The collection optical elements collect light from the sample and transmit the collected light to a detector. None of the collection optical elements are included among the illumination optical elements. The device forming an aperture limits detection of light from the sample to light associated with a limited vertical depth within the sample, and is one of the collection optical elements.

62 Claims, 12 Drawing Sheets

U.S. PATENT DOCUMENTS

| | | | |
|---|---|---|---|
| 4,162,405 A * | 7/1979 | Chance et al. .............. 424/9.6 |
| 4,556,903 A | 12/1985 | Blitchington et al. |
| 4,855,930 A | 8/1989 | Chao et al. |
| 4,893,008 A | 1/1990 | Horikawa |
| 4,968,892 A | 11/1990 | McAtee |
| 5,200,819 A | 4/1993 | Nudelman et al. |
| 5,310,674 A | 5/1994 | Weinreb et al. |
| 5,338,753 A | 8/1994 | Burstein et al. |
| 5,355,215 A | 10/1994 | Schroeder et al. |
| 5,483,546 A | 1/1996 | Johnson et al. |
| 5,485,530 A | 1/1996 | Lakowicz et al. |
| 5,506,141 A | 4/1996 | Weinreb et al. |
| 5,578,832 A | 11/1996 | Trulson et al. |
| 5,585,639 A | 12/1996 | Dorsel et al. |
| 5,597,696 A | 1/1997 | Linn et al. |
| 5,631,169 A | 5/1997 | Lakowicz et al. |
| 5,713,364 A | 2/1998 | DeBaryshe et al. |
| 5,718,915 A | 2/1998 | Virtanen et al. |
| 5,807,522 A | 9/1998 | Brown et al. |
| 5,815,278 A | 9/1998 | Johnston et al. |
| 5,832,931 A | 11/1998 | Wachter et al. |
| 5,973,828 A | 10/1999 | Webb |
| 5,997,861 A | 12/1999 | Virtanen et al. |
| 6,030,581 A | 2/2000 | Virtanen |
| 6,097,485 A | 8/2000 | Lievan |
| 6,104,945 A | 8/2000 | Modell et al. |
| 6,118,580 A | 9/2000 | Webb |
| 6,187,267 B1 | 2/2001 | Taylor et al. |
| 6,196,979 B1 | 3/2001 | Virtanen |
| 6,197,534 B1 | 3/2001 | Lakowicz et al. |
| 6,252,236 B1 | 6/2001 | Trulson et al. |
| 6,274,373 B1 | 8/2001 | Virtanen |
| 6,310,687 B1 | 10/2001 | Stumbo et al. |
| 6,312,901 B2 | 11/2001 | Virtanen |
| 6,322,682 B1 | 11/2001 | Arvidsson et al. |
| 6,327,031 B1 | 12/2001 | Gordon |
| 6,331,275 B1 | 12/2001 | Virtanen |
| 6,342,349 B1 | 1/2002 | Virtanen |
| 6,351,325 B1 | 2/2002 | Mandella et al. |
| 6,369,928 B1 | 4/2002 | Mandella et al. |
| 6,379,699 B1 | 4/2002 | Virtanen et al. |
| 6,384,951 B1 | 5/2002 | Basiji et al. |
| 6,395,556 B1 | 5/2002 | Lakowica et al. |
| 6,403,947 B1 | 6/2002 | Hoyt et al. |
| 6,406,293 B1 | 6/2002 | Burstein |
| 6,414,779 B1 | 7/2002 | Mandella et al. |
| 6,423,956 B1 | 7/2002 | Mandella et al. |
| 6,441,356 B1 | 8/2002 | Mandella et al. |
| 6,454,970 B1 | 9/2002 | Ohman |
| 6,459,484 B1 | 10/2002 | Yokoi |
| 6,462,809 B1 | 10/2002 | Ryan et al. |
| 6,503,359 B2 | 1/2003 | Virtanen |
| 6,509,161 B1 | 1/2003 | Barker et al. |
| 6,566,069 B2 | 5/2003 | Virtanen |
| 6,603,537 B1 | 8/2003 | Dietz et al. |
| 6,620,478 B1 | 9/2003 | Ohman |
| 6,632,656 B1 | 10/2003 | Thomas et al. |
| 6,653,625 B2 | 11/2003 | Andersson et al. |
| 6,710,316 B2 | 3/2004 | Mandella et al. |
| 6,713,742 B2 | 3/2004 | Mandella et al. |
| 6,717,136 B2 | 4/2004 | Andersson et al. |
| 6,728,644 B2 | 4/2004 | Bielik et al. |
| 6,811,736 B1 | 11/2004 | Ohman et al. |
| 6,812,456 B2 | 11/2004 | Andersson et al. |
| 6,812,457 B2 | 11/2004 | Andersson et al. |
| 6,825,928 B2 | 11/2004 | Liu et al. |
| 6,947,127 B2 * | 9/2005 | Wolleschensky et al. ...... 356/73 |
| 7,576,862 B2 * | 8/2009 | Cromwell et al. ........... 356/445 |
| 2001/0052976 A1 | 12/2001 | Juncosa et al. |
| 2002/0055179 A1 | 5/2002 | Busey et al. |
| 2003/0030850 A1 | 2/2003 | Heffelfinger et al. |
| 2003/0044967 A1 | 3/2003 | Heffelfinger et al. |
| 2004/0071332 A1 | 4/2004 | Bruce et al. |
| 2005/0046849 A1 | 3/2005 | Cromwell et al. |

FOREIGN PATENT DOCUMENTS

| | | |
|---|---|---|
| GB | 2076962 | 12/1981 |
| WO | WO 97/26539 | 7/1997 |
| WO | 00/43780 | 7/2000 |
| WO | WO 00/71991 | 11/2000 |
| WO | WO 00/71991 A | 11/2000 |
| WO | WO 01/35079 | 5/2001 |
| WO | WO 02/35474 A | 5/2002 |
| WO | 2004/017374 A2 | 2/2004 |
| WO | WO 2004/017374 A2 | 2/2004 |

OTHER PUBLICATIONS

Heather Thompson, "Compact Discs May Play a Role in Diagnosis," Jul. 2004, MDDI.

Chad Boutin, "BioCDs could hit No. 1 on Doctors' charts," May 18, 2004, Purdue News.

"Products: Optical LiveCell™ Array," Molecular Cytomics, http://www.molecular-cytomics.com/LiveCell.htm, downloaded Apr. 28, 2005.

Manoj M. Varma et al., "High-Speed Label-Free Multi-Analyte Detection through Micro-interferometry," Proceedings of SPIE vol. 4966, SPIE, 2003.

U.S. Office Action mailed Jan. 29, 2007, from U.S. Appl. No. 10/928,484.

Lakowicz et al., "Anisotropy-Based Sensing with Reference Fluorophores," Oct. 20, 1998, Analytical Biochemistry 267, 397-405 (1999).

Chad Boutin, "BioCDs could hit No. 1 on doctos' charts," May 18, 2004, Purdue News.

Manoj M. Varma[*a] et al., "High-Speed Label-Free Multi-Analyte Detection through Micro-interferometry," Proceedings of SPIE vol. 4966, SPIE, 2003.

International Search Report dated May 4, 2006 from related International Application No. PCT/US05/23520.

Office Action dated Oct. 6, 2006 from U.S. Appl. No. 10/927,748.
Office Action dated Apr. 23, 2007 from U.S. Appl. No. 10/927,748.
Office Action dated Aug. 27, 2007 from U.S. Appl. No. 10/927,748.
Office Action dated Jan. 29, 2007 from U.S. Appl. No. 10/928,484.
Office Action dated Jul. 30, 2007 from U.S. Appl. No. 10/928,484.
Office Action dated Feb. 5, 2008 from U.S. Appl. No. 10/928,484.
Office Action dated May 16, 2008 from U.S. Appl. No. 10/928,484.
Office Action dated Sep. 30, 2008 for corresponding European Patent Application No. 04786593.6.
Notice of Allowance and allowed claims for U.S. Appl. No. 10/928,484, mailed Dec. 23, 2008.
Summons to Attend Oral Proceedings dated May 31, 2010 for corresponding European Patent Application No. 04786593.6.
Office Action dated May 25, 2010 for corresponding Japanese Patent Application No. 2006-524881.

* cited by examiner

TIME DEPENDENT FLUORESCENCE MEASUREMENTS

CROSS REFERENCE TO RELATED APPLICATIONS

This application is a continuation of U.S. patent application Ser. No. 10/927,748, filed on Aug. 26, 2004, and entitled "TIME DEPENDENT FLUORESCENCE MEASUREMENTS" which claims benefit of U.S. Provisional Patent Application No. 60/497,803, filed Aug. 26, 2003, entitled "LASER SCANNING METHOD FOR TIME DEPENDENT MEASUREMENT OF FLUORESCENCE," and of U.S. Provisional Patent Application No. 60/497,764, also filed Aug. 26, 2003, and entitled "LASER SCANNING SYSTEM FOR TIME DEPENDENT MEASUREMENT OF FLUORESCENCE," each of which are hereby incorporated by reference herein.

BACKGROUND

This invention relates to measuring fluorescence and properties derived from fluorescence in materials.

In conventional fluorescence microscopy, a sample, such as a biological specimen is stained with fluorophores before being illuminated by light of a relatively short wavelength. The illumination light, which typically is provided from a laser, excites the fluorophores into a higher energy state where they remain for a short period of time, before returning to their original energy state while emitting fluorescent light of a wavelength longer than the excitation wavelength. In a fluorescence microscope, the emitted fluorescent light is collected by an objective lens of the microscope and is passed through the optical system of the microscope, such that it can be viewed by a user, for example, through the eyepieces of the microscope, or on a display screen of a video system that is connected to the microscope's optical system. In many cases, both the excitation light and the fluorescent light share an optical path through the microscope's optical system, and can be separated as needed, by optical components such as dichroic mirrors that reflect light above the excitation wavelengths while passing the excitation light.

The systems that have found most use in laboratories generally use visible fluorescence of materials and visible light sources. The spatial resolution that can be obtained is determined by the specific optical setup. In some cases, the laboratory experimental setups use pulsed laser light to improve the quality of the fluorescence image. Laboratory arrangements are often used to detect biomolecular reactions and interactions that can be probed by fluorescent methods. Fluorescent dyes are commonly used to examine cells by staining portions of the cells. For more routine imaging analyses, or assays, the excitation light source can illuminate a portion of an object to be examined, such as one microlocation in an array of microlocations.

For reasons of image contrast or signal discrimination, there is often a need to improve the resolution and eliminate background noise in the focal region of the sample that is being studied, as biological samples in particular are fairly transparent and light collection over a too wide depth of focus may obscure the specific details that are being studied of the biological sample. Current solutions to this problem include confocal laser scanning microscopy or wide-field deconvolution technologies, which generate optical "slices" or cross-sections that include only the in-focus information. Another technique is the use of two-photon (2P) excitation produced by an infrared ultra-short, pulsed laser beam. In two-photon systems, the pulsed laser allows the same fluorophores to be excited by photons of twice the wavelength than those used in single photon systems, but the longer wavelength photons are not absorbed by the biological sample, which results in decreased toxicity to living cells and decreased photo bleaching. Furthermore, the infrared wavelength excitation significantly reduces scattering within the tissue, as the scattering coefficient is proportional to the inverse fourth power of the excitation wavelength, resulting in penetration deeper into the specimen.

Fluorescent systems of this kind typically work well in laboratory settings. However, in the chemical and biotechnology industry, there is often a need to analyze a large number of samples in a time and cost-efficient manner, and due to the different requirements in these environments, the above configurations are often not suitable or possible to use. Therefore, what is needed is an improved apparatus that can be used to analyze an array of samples or objects in an efficient manner, while having the ability to discriminate against background noise.

SUMMARY

In general, in one aspect, the invention provides methods and apparatus, including computer program products, implementing and using techniques for collecting optical data pertaining to one or more characteristics of a sample. The apparatus has a light source, one or more illumination optical elements, a scanner, one or more collection optical elements, and a device forming an aperture that limits detection of light from the sample. The illumination optical elements direct a light beam from the light source onto the sample. The scanner scans the light beam across the sample. The one or more collection optical elements collect light from the sample and transmit the collected light to a detector. None of the one or more collection optical elements are included among the one or more illumination optical elements. The device forming an aperture limits detection of light from the sample to light associated with a limited vertical depth within the sample, and is one of the collection optical elements.

Advantageous embodiments can include one or more of the following features. The device forming the aperture can be a slit aperture. The device forming the aperture can be a bundle of optical fibers. Light entering different optical fibers in the bundle of fibers can correspond to light at different vertical depths within the sample. The collection optical elements can collect light from a scan line on the sample with substantially uniform efficiency. The collection optical elements can include a cylindrical lens or a spherical lens.

Two or more detectors can be offset from one another with respect to a path for collecting the light from the sample, wherein each of the two or more detectors can be positioned to capture light being emitted from a different vertical depth within the sample. There can be logic for adjusting the position of the sample with respect to the collection optical elements in response to light intensity detected at the two or more detectors to maintain a substantially uniform vertical depth from position to position on the sample. The detector can include a photomultiplier detector, a photodiode device, a charge coupled device, or a microchannel plate. Two or more detectors can be provided that receive light from the same region of the sample and detect two or more different characteristics of the sample, such as different polarizations of the light, different frequencies of the light and different lifetimes. Logic can be provided for examining the correlation between the signals obtained from the two or more detectors to identify objects and exclude background noise.

The collection of optical data can be limited to regions of the sample known or detected to hold particular objects to be characterized on the sample, and the logic can be implemented in computer software or computer hardware instructions that can be read and executed by a processor operatively connected to the detector. The logic for limiting collection of optical data can limit collection by only recording optical data when an intensity of the collected light is above a certain adjustable threshold value and the optical data meets at least one additional criterion. The logic for limiting collection of optical data can limit collection by only recording optical data during time periods when the beam from the light source is scanned across an area of interest on the sample.

The light source can be a continuous wave laser, a pulsed laser, a mode-locked high repetition rate laser, or a Q-switched laser. The continuous wave laser can be a diode laser, a diode-pumped solid state laser, a gas laser, or a tunable solid state laser system and can be modulated in the frequency range of 1 kilohertz to 2 Gigahertz. The pulsed laser can be configured to emit pulses in a frequency range of 1 Hertz-100 Megahertz with a spacing ranging from 10 nanoseconds to 1 second. The mode-locked laser can have a repetition rate that is higher than or equal to 10 Megahertz. The Q-switched laser can be pulsed at a frequency in the range of 1 Hertz to 1 Megahertz. The light beam emitted from the light source can be intensity modulated in time with a frequency in the range of 1 Hertz to 2 Gigahertz.

The scanner can include one or more polygonal mirrors being rotated by a scanning element to scan the light beam across the sample. The scanner can include one or more mirrors being moved by a galvanometer to scan the light beam across the sample. The scanner can be a resonant mirror scanner. The one or more illumination optical elements can include a telecentric lens.

In general, in another aspect, the invention provides methods and apparatus, including computer program products, implementing and using techniques for collecting optical data pertaining to one or more characteristics of a sample. The apparatus has a light source, one or more illumination optical elements, a scanner, and one or more collection optical elements. The illumination optical elements direct a light beam from the light source of a first frequency onto the sample. The scanner scans the light beam across the sample. The collection optical elements collect light of a second frequency from the sample and transmit the light to a detector. None of the one or more collection optical elements are included among the one or more illumination optical elements.

In general, in another aspect, the invention provides methods and apparatus, including (computer program products, implementing and using techniques for collecting optical data pertaining to one or more characteristics of a sample. The apparatus has a light source, one or more illumination optical elements for directing a light beam from the light source onto the sample, a scanner for scanning the light beam across the sample, one or more collection optical elements, a first device that limits detection of light from the sample to light associated with a first vertical depth within the sample, and a second device that limits detection of light from the sample to light associated with a second, different, vertical depth within the sample, where the first and second devices are collection optical elements.

Advantageous embodiments can include one or more of the following features. Logic can be included for automatically adjusting the vertical position of the sample with respect to the collection optical elements in response to the relative light intensity collected at the first and second devices in order to maintain a consistent vertical position of the sample with respect to the collection optical elements during scanning. At least one of the first device and the second device can be an optical fiber. The first device can include a first row of optical fibers and the second device can include a second row of optical fibers. The one or more detectors can include one or more microchannel plates arranged to separately detect light from the first and second devices. The one or more detectors can include a photomultiplier detector, a photodiode device, a microchannel plate, or a charge coupled device. Two or more detectors can be included for receiving light from the sample and detecting two or more different characteristics of the light from the sample. The light beam from the light source can be monochromatic having a first wavelength and wherein one or more of the collection optics and the one or more detectors is tuned to collect light at a second wavelength, which is different from the first wavelength. A third device can be included that limits detection of light from the sample to light associated with a third, different, vertical depth within the sample.

The invention can be implemented to include one or more of the following advantages. Improved system and methods for cell and microarray analysis are provided. The use of a scanning light source, in combination with improved geometry of the optical collection system, allows for many samples or objects to be illuminated in a single scan. Furthermore, the samples emit radiation in a specific confined region that is amenable to detection with characteristics that allow a higher degree of spatial resolution compared to several existing systems. The use of separate illumination optical components and separate collection optical components reduces the need to separate the illumination light from the fluorescent light emitted by the illuminated sample, and thus provides a simpler and more robust configuration. Using a cylindrical lens, such as a rod lens as one of the collection optical elements allows collection of an entire scan line with substantially uniform efficiency.

The polarized nature of the light source can be used to examine reactivity, environment, and/or biological activity of either native material or material that has been tagged with a fluorescent marker.

In one embodiment, the pulsed or modulated nature of the system allows for time dependent, rapid determination of chemically or photo-induced bioactivity. The timing of the pulses, and the timing of the responses can be used to extract physical information, such as fluorescence lifetimes and polarization relaxation times, as well as chemical or biological information. With determinable characteristics of time resolution coupled with the scanning feature, time-dependent information can be extracted, which can allow for precise mapping into a spatial domain. The optical detection system confines the detection region in such a way that an entire array can be scanned with a precisely located detection region without requiring a conventional autofocus mechanism for the collection optics with the attendant timing requirements. By using an apparatus that allows for improved light collection efficiency and background discrimination, the scanning source focus stays within the confined detection region. These characteristics of the invention allow for mapping to a microlocation, either at the subcellular level or at a macro position within a microarray for rapid assay analyses.

The output signal is uniquely suited to analyzing the fluorescence of cells and other objects or features within cells or in solution. The output signal and its characteristic behavior can be analyzed to determine structural, chemical, or biological properties of the object. An image of each object can be spectrally and/or temporally decomposed to discriminate object features by using polarization, fluorescence lifetime, or rotational correlation time as required. An object being imaged in accordance with the present invention can be stimulated into fluorescence, either by autofluorescence, or by binding a molecule or probe, that can be stimulated to fluoresce. Morphological and spectral characteristics of cells and sub-cellular features can be determined by measuring fluorescence signals that may also include time dependent spectral information, which can be used to determine time dependent cellular responses or other information about the cells and their components. Similar measurements can be used to determine nuclear fluorescence intensity, cytoplasm fluorescence intensity, background autofluorescence intensity, fluorescent depolarization intensity, and the ratios of any of these values.

The output signal can also be used to monitor the sample's position, and if necessary readjust the position of the sample, such that an optimal amount of light is collected. The output signal can also be used to reduce the data storage requirements, for example, by only storing data when the intensity of the collected fluorescent light is above a certain threshold value.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
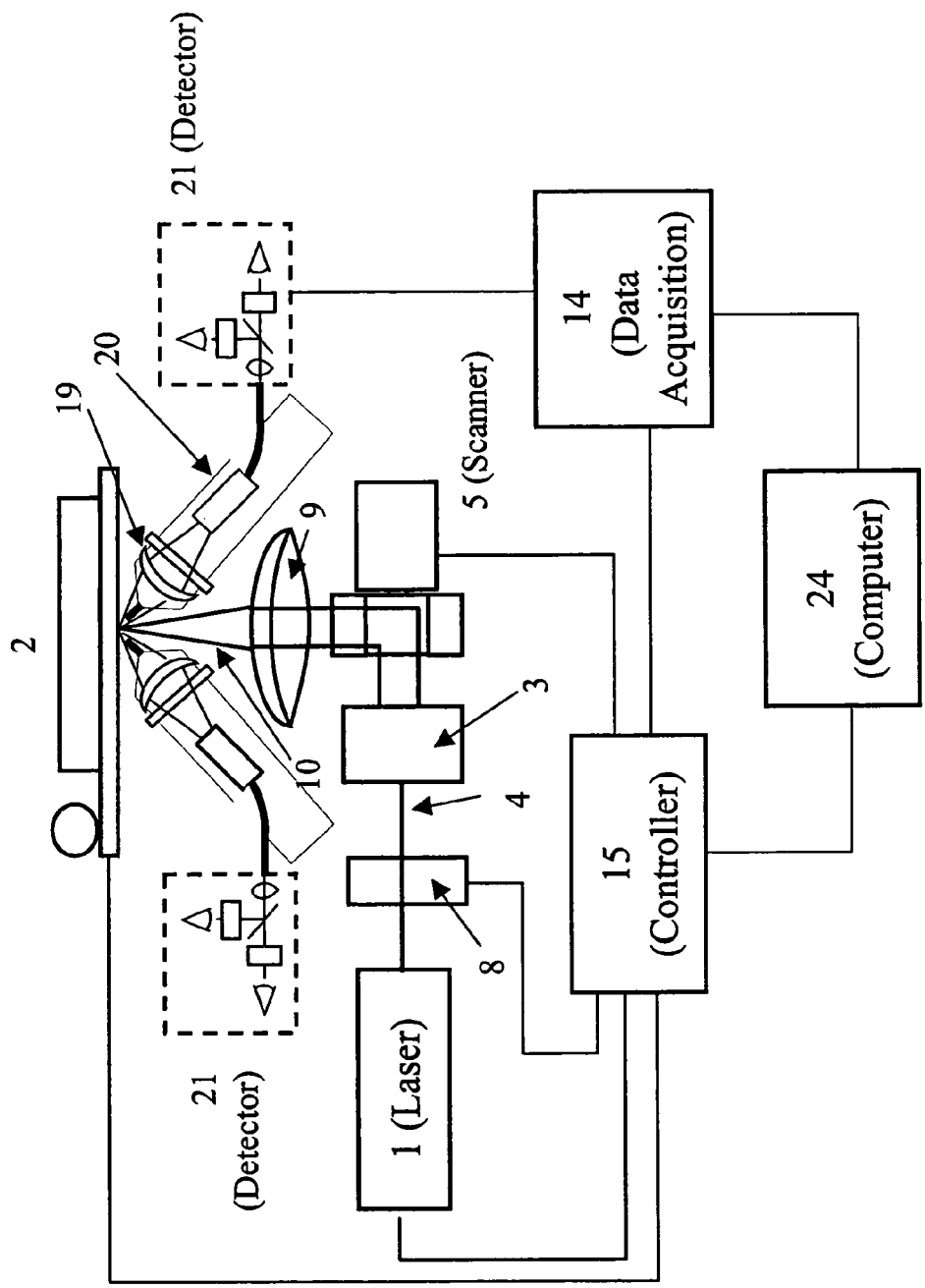
FIG. 1 is a schematic view of an apparatus for collecting optical data in accordance with a first embodiment of the present invention.

The invention provides an improved apparatus that uses a scanning light source, which can be focused onto an array of samples or objects, with the ability to discriminate against background noise or signal, and makes use of image contrast mechanisms. The apparatus of the invention can be operated in several distinct modes or combinations thereof, depending on what type of sample data needs to be collected. A high-level description of some exemplary modes will first be provided, followed by a more detailed discussion about the parts and geometry of the apparatus.

In a first mode, the output signal from the apparatus contains information such as the number of discrete positions in a cell or other object from which the fluorescent light originates, the relative location of the signal sources, and the color (e.g., wavelength or waveband) of the light emitted at each position of the object. As a result of the geometry of the illumination optics, a relatively large illumination region is created that is confined to a region within the sample volume, thereby eliminating the need to have an apparatus which must adjust the focus of the illumination continuously and an in real time over a plurality or an array of samples. The geometry of the collection optics limits the detection region to a focal volume where the sample is contained and from which the data is collected. In one embodiment, multiple collection arrangements are used with the attendant benefits, which will be described below for a setup with two collection lenses.

In a second mode, a plane-polarized laser beam can be propagated through the optical system onto the sample, allowing interrogation of the biological material with polarized light. In this mode the emitted light can be separated into its two orthogonal components and analyzed either sequentially in time with a switchable modulator, such as an electrooptic modulator, to allow for detection of the parallel and perpendicular components, or simultaneously with multiple collection optics with specified perpendicular and parallel polarizing filters. The polarized nature of the excitation source allows for measurement of properties of biological materials where the characteristics of the anisotropy of the emission, or the time dependent nature of the relaxation of the polarization, can give rise to spatial or physical information about the biological moiety.

In a third mode, several laser beams can be propagated through the optical system onto the sample allowing interrogation of the biological material with different wavelengths of light or with the same wavelength at different times. In this mode the lasers can be pulsed simultaneously or with a fixed or variable delay between pulses. Delay between pulses allows for measurement of properties of biological materials in an excited state where the first laser pulse causes excitation of the biological moiety and the second or additional laser pulses interrogate that moiety in an excited state. The laser beams can be co-propagated so that they focus on the same sample area during a scan or, alternatively, they can be propagated at some relative angle so that during a scan the laser beams sequentially move over the same sample area.

In a fourth mode, a single modulated laser beam can be propagated through the optical system onto the sample allowing lifetime measurements of the fluorescence in the biological material.

In a fifth mode, several detectors can be used in conjunction with one collection optics arrangement, which creates multiple confinement regions for analysis, the advantages of which will be described in further detail below.

In a sixth mode, several collection optics arrangements can be used to provide improved confinement over a single collection optic with the unique geometry, or can be used to collect emission from the confined region with several characteristics which are uniquely specified to each collecting optics, the advantages which will be described below.

The apparatus will now be described in further detail, by way of example, with reference to FIGS. 1-11. As shown in FIG. 1, in one embodiment, an excitation light source (1) emits excitation light (4) to be projected onto a sample (2) that is to be investigated and which rests on a microarray plate. Typically, the excitation light source (1) is a laser, such as an Ar or Ar/Kr mixed gas laser with excitation lines of 488, 514, 568 and 647 nm. In one embodiment, a continuous wave (CW) laser, such as the Compass 315 M laser from Spectraphysics Inc. of Mountain View, Calif., is used as an excitation source. Depending on the laser (1) and specific optics used in the apparatus, the wavelength of the excitation light can be either within the visible range (i.e., 400-700 nm), or outside the visible range. For excitation wavelengths below 400 nm photochemical reaction rates, such as those due to photobleaching, tend to be substantial. In one embodiment, the output from the laser (1) can be modulated and give information about the time dependent response of fluorescence signals by using a frequency modulation detection scheme. In another embodiment, a pulsed laser with laser pulses of approximately 12 ps FWHM (Full Width at Half Max) with a spacing of approximately 12 ns is used as the excitation light source (1). The average power of the laser (1) at the sample (2) is typically in the range 1 mW-1 W. The spacing of 12 ns is convenient for fluorescent lifetime detection, but can be varied as necessary, for example, by varying the cavity length of the laser (1). Common to both embodiments is the use of time-resolved imaging as a contrast producing agent. This has been developed significantly in the field of fluorescence microscopy and has been described in detail by Marriott, Clegg, Arndt-Jovin, and Jovin, 1991, Biophys. J. 60:1374-1387; Verveer, Squire, and Bastiaens, 2000, Biophys. J. 78:2127-2137; Buehler, Dong, So, French, and Gratton, 2000, Biophys. J 79:536-549; Fushimi, Dix, and Verkman, 1991, Biophys. J. 57, 241-254; and Berndt, Gryczynski, and Lakowicz, 1993, U.S. Pat. No. 5,196,709; as well as others not referenced herein. The apparatus and methods used for such studies can generally be classified as one of two types: time-domain or frequency-domain (see Hanley, Subramaniam, Arndt-Jovin, and Jovin, 2001, Cytometry 43:248-260). These apparatus and methods are well-known to those skilled in the art.

After leaving the laser (1), the excitation light (4) passes through one or more illumination optical elements to the sample (2). The illumination optical elements include an electro-optic modulator (8), a set of beam-shaping lenses (3), a scanning device (5), and a multi-element lens (9). The electro-optic modulator (8) can be used to polarization modulate the excitation light (4), if required by the investigation that is to be carried out on the sample (2). The set of beam-shaping lenses (3) expands the laser beam in order to match the input aperture of the scanning lens and provide the desired illumination region size at the sample (2). The scanning device (5) moves the expanded laser beam back and forth in a line-scan over the sample (2) after the beam has been focused by the multi-element lens (9). The scanning device (5), which will be described in further detail below, can be an electromechanical device coupled to an optic element, such as a mirror driven by a galvanometer. In one embodiment, which will also be described in further detail below, the scanning device (5) uses a polygon with multiple reflective surfaces to scan the laser beam across the sample (2). The multi-element lens (9) is designed to focus the laser light at the operating wavelength of the laser (1). The multi-element lens (9) can, for example, be a microscope objective designed for the operating wavelength or a specially designed scanning lens, such as a telecentric lens, that has appropriate parameters to achieve a flat focal plane, for example, with a long working distance and low first and second order aberrations, thus producing the same spot size and shape over a wide range of positions (such as a scan line). The telecentric lens is particularly useful for covering a large field of view.

After passing the multi-element lens (9), the beam (10) is focused onto a region of the sample (2) to be imaged. The focal region is located above, for example, a base of a microarray plate. The sample (2) can be objects to be interrogated by fluorescence, such as cells attached to the bottom of a microwell of the microarray plate.

The fluorescent light emitted by the sample (2) is collected by one or more collection optical elements (19). As will be discussed below, there are several ways to configure the collection optical elements (19) that allow scanning of a large array, such as microarray plate. In one embodiment, the collection optical elements (19) is a rod lens, designed to capture the entire range of sweep of the beam (10) over one dimension of the base (11) of the sample array. The collection optical elements (19) can also include other types of lenses, or an aggregate of lenses, as would be determined by the specific information required from the emission. In some embodiments, multiple setups of collection optical elements (19) can be used to improve collection efficiency.

The light collected by the collection optical elements (19) is transmitted to a detector (21) located at a convenient distance from the collection optical elements (19). The transmission of the fluorescent light can be accomplished by, for example, an optical fiber or a bundle of optical fibers (20). In one embodiment, the detector (21) is a detector with high gain, such as a photomultiplier tube, which produces an electrical output signal. The electrical output signal is further processed by a data acquisition system (14), which performs operations such as optimization of the gain and the signal to noise ratio (S/N), by making use of signal enhancing, averaging, or integrating detection systems.

Figure 2:
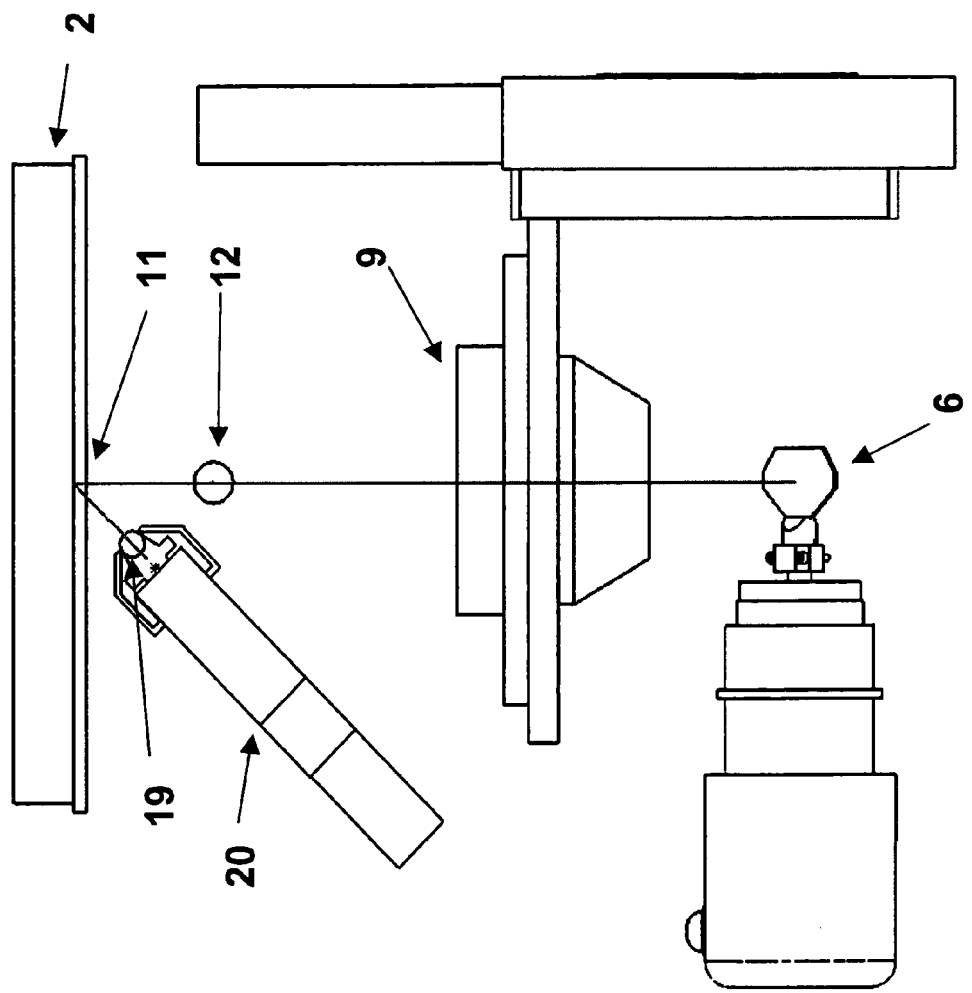
FIG. 2 is a side elevational view of a first embodiment of a scanner part of the apparatus shown in FIG. 1.
Figure 3:
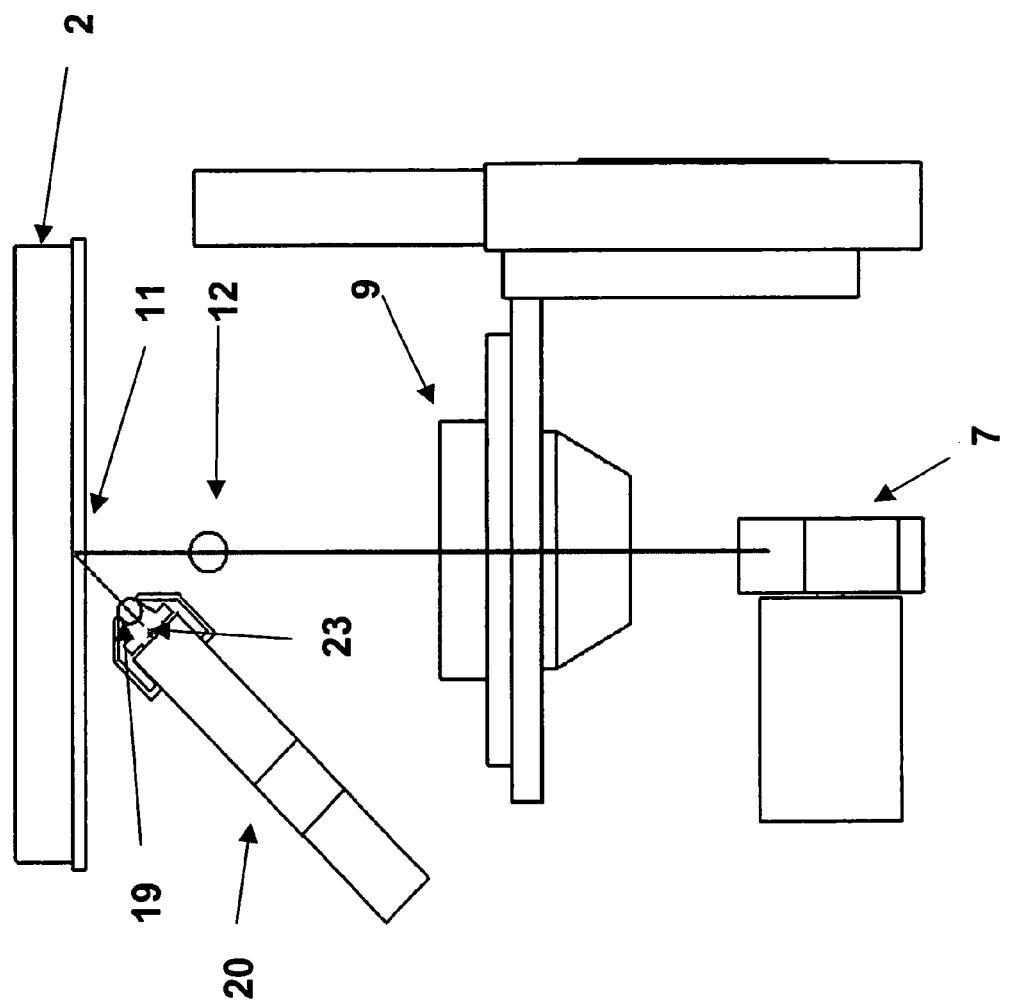
FIG. 3 is a side elevational view of a second embodiment of a scanner part of the apparatus shown in FIG. 1.
Figure 4:
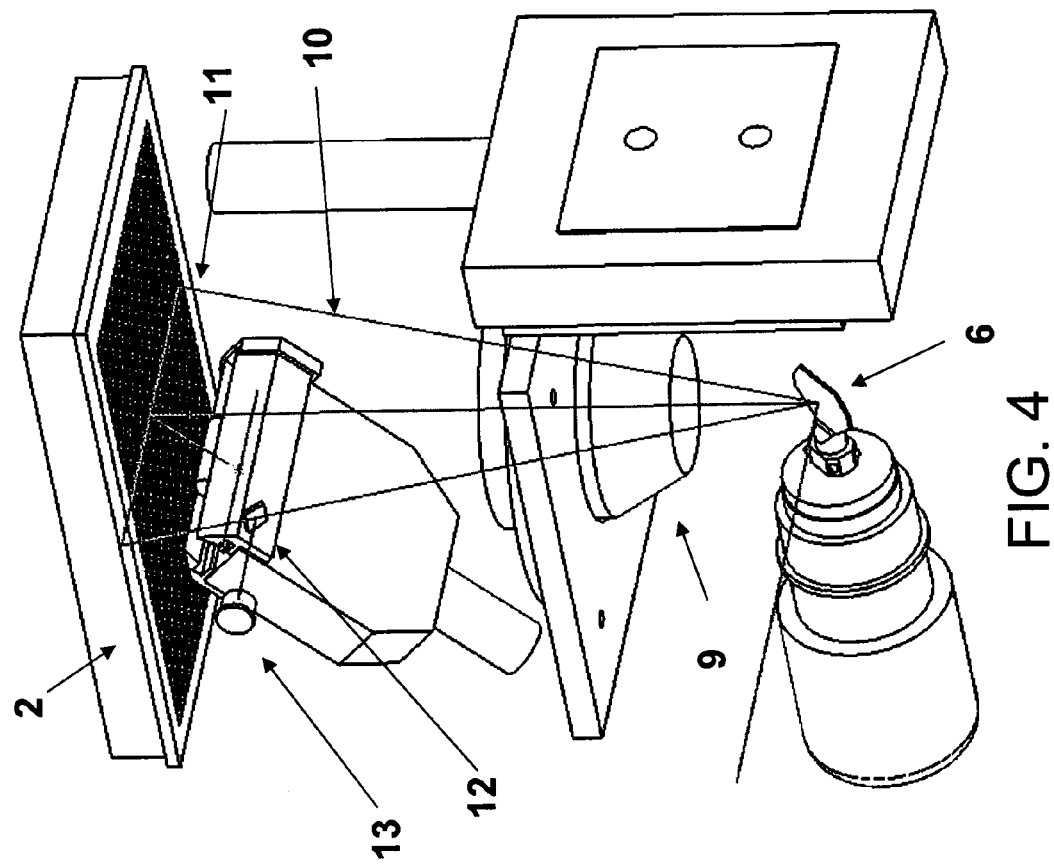
FIG. 4 is an isometric view of the scanner part shown in FIG. 2.
Figure 5A:
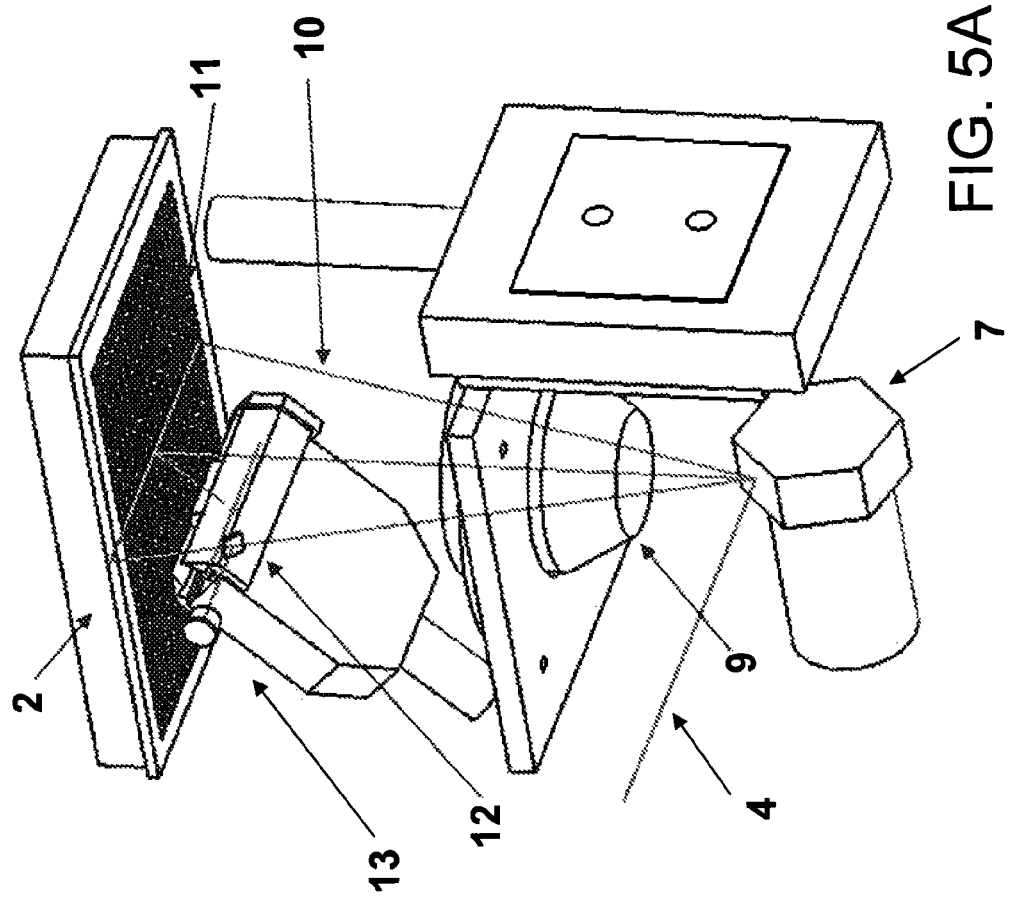
FIG. 5A is an isometric view of the scanner part shown in FIG. 3.
Figure 5B:
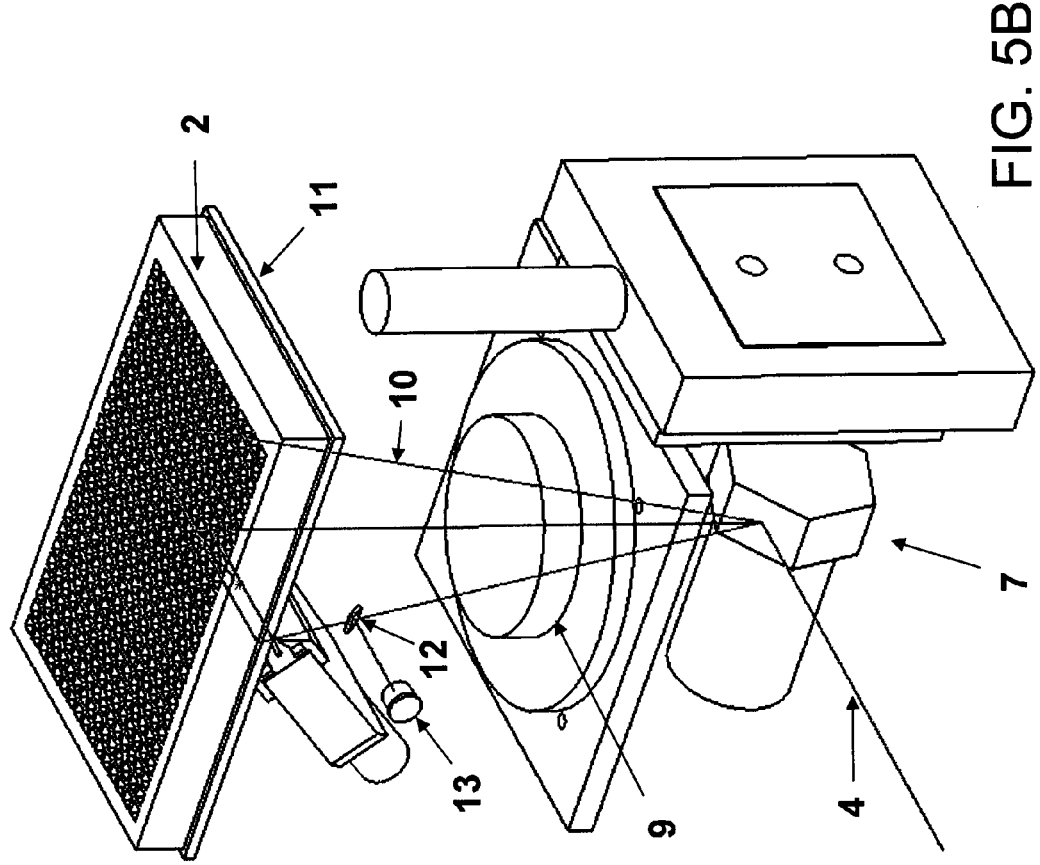
FIG. 5B is an isometric view of an apparatus for collecting optical data in accordance with the invention, with an alternative embodiment of the sample array.

FIG. 2 shows a side elevational view of the scanning portion of a first embodiment of an apparatus in accordance with the invention. FIG. 4 shows an isometric view of the scanning portion of the same embodiment of the apparatus. In the embodiment show in FIGS. 2 and 4, the scanning device (5) is a mirror (6) driven by a galvanometer. By moving the mirror (6) back and forth using the galvanometer, the excitation light (10) from the laser (1) can be swept across the sample (2). FIGS. 3, 5A and 5B show similar views of a second embodiment of an apparatus in accordance with the invention, where the scanning device (5) instead is a polygon (7) with multiple reflective surfaces. In this embodiment the laser beam (10) is swept over a region of the sample (2) by rotating the polygon (7). In yet another embodiment, the scanning device (5) is a resonant scanning device, such as a mirror mounted on a torsion bar with electromagnets causing the mirror to move back and forth. In all embodiments, the beam velocity across the sample (2) is thus a result of the rotation speed of the polygon (7) or the sweep velocity of the galvanometer and the resonant scanning device, respectively. Each of the different configurations has different advantages and drawbacks. For example, the galvanometer is less expensive than the polygon mirror, but operates at a smaller angle and at a lower frequency, which causes a slower scanning speed. The resonant scanning device is cheaper than both the galvanometer and the rotating mirror and operates at larger angles, but only operates at a predetermined frequency. The beam motion at the focal plane in the sample (2) is typically 1-10 mm/ms, but can be as fast as 10-1000 mm/ms, depending on the sweep velocity of the mirror (6), or the rotation speed of the polygon (7). The polygon (7) is typically rotated at rotation speeds from 0.5 kHz to 20 kHz.

The multi-element lens (9) that receives the laser light (4) is designed to focus the laser light at the operating wavelength of the laser (1). The multi-element lens (9) focuses the laser light (4) close to the diffraction limit of the multi-element lens (9), which is typically in the range of 5-20 microns, but can be as small or large as 1-200 microns. The sample or sample array (2) is arranged to accept the focused, beam at, or just above, the base (11) of the sample (2). The length of the scan line across the sample array (2) can be varied and is typically in the range 5 mm to 100 mm. In one embodiment, the scan light (10) can interrogate for example, a 96-well plate in less than one minute at 5 micron resolution.

As can be seen in FIGS. 2-5, an optical element (12), such as a mirror, is provided approximately half way between the scan lens and the sample to intercept and reflect a section of the incident light (10) onto a detector (13). Typically, the reflector (12) is located about 1-2 cm from the scan lens. The detector (13) is used to detect the location of the start of scan, in order to trigger the data acquisition system (14), which will be described in further detail below. The detector (13) can, for example, be a photodiode or equivalent component that can sense the incoming light (10) reflected from the reflector (12) and provide an electrical signal to the data acquisition system (14). A second mirror and detector can be placed on the other side of the scan line to detect the end of a scan and thereby enable bidirectional scanning.

Figure 7:
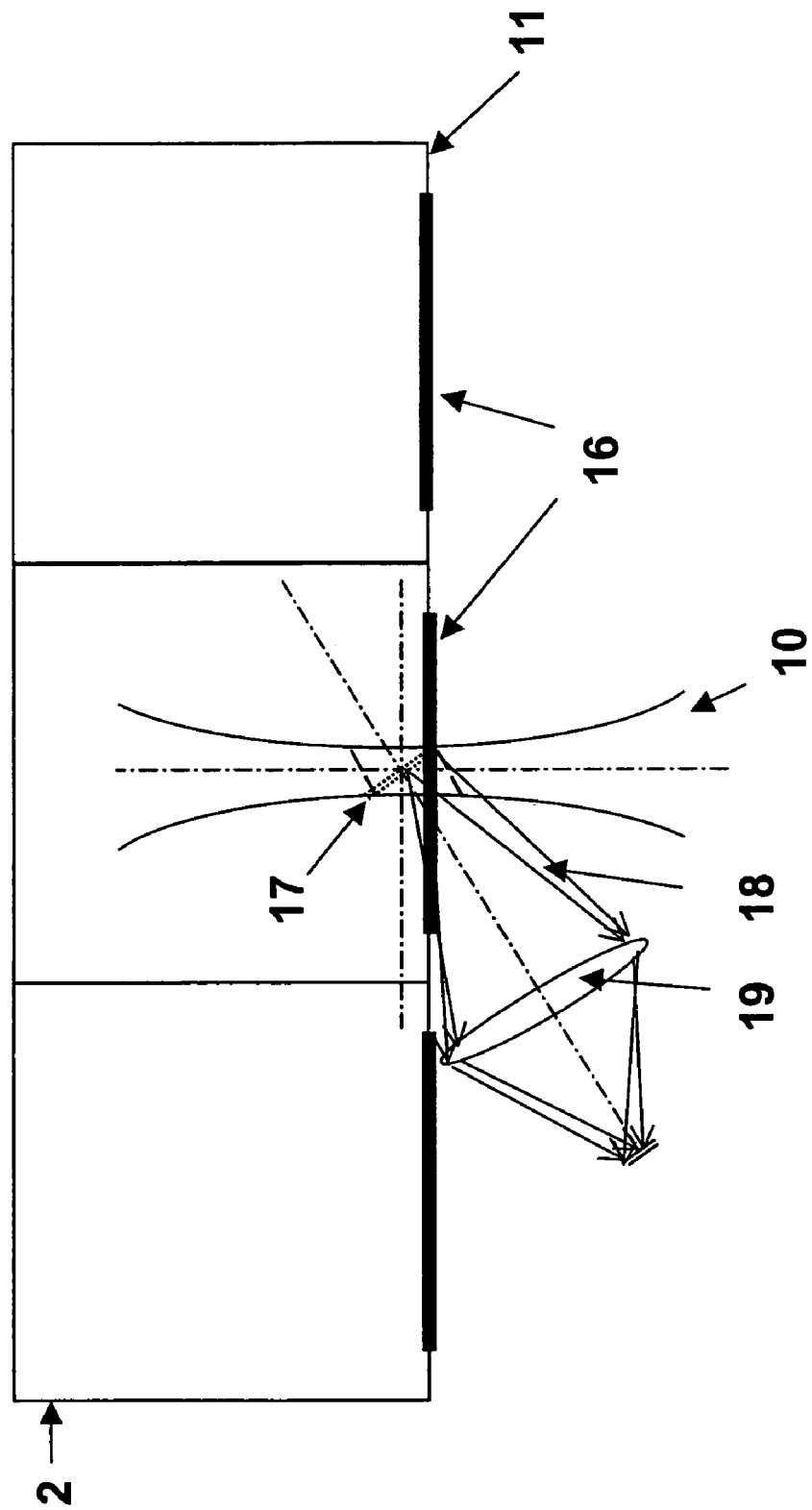
FIG. 7 is a schematic diagram showing a confined field of view for a single detector configuration of the apparatus of FIG. 1.

FIG. 7 shows an enlarged view of the sample (2), how incoming light (10) illuminates the sample (2), and a source region (17) from which the fluorescent light is collected in a single detector embodiment of the apparatus of FIG. 1. The sample (2) is located on a base (11) with a series of optical elements (16) that allow the laser light (10) to be transmitted through to the sample contained in the array. The array can, for example, be a microarray plate containing wells with solutions or samples adhered to the bottom of the wells. The focal plane location is near the inner side of optical elements (16) and defines the region of highest light flux, thereby defining a region of highest emitted light source. The region's volume size depends on the multi-element lens (9) configuration and the depth of the interrogated sample (2) located above the base (11). The defined volume of a source region (17), which actually gives rise to the fluorescent signal, additionally depends on the configuration of the collection optical elements (19), as will now be discussed.

As can be seen in FIG. 7, the geometry of the collection optical elements (19) is such that the collection region is confined to the region of the field of view for the detector (21). The fluorescent signal intensity is confined to a source region (17) formed by the intersection of the excitation source's focal region and the image of the detector (21) inside this region, as shown in FIG. 7. The source region is located within a limited vertical depth of the sample, that is, at a limited distance range above the base (11) upon which the sample (2) rests. A number of advantages result from arranging the collection optical elements (19) such that a collection path (18) forms an angle with the incident light (10). Another advantage is the elimination of the need for optically flat micro arrays that do not deviate in the location of surface apertures (16) of the well (2). The collection region is fixed or confined by the collection optical elements (19) configuration so as to not be out of the focal plane of the system. Yet another advantage is that signal discrimination from background fluorescence in the sample well is much higher than that obtained by a parallel collection system without eliminating or filtering the fluorescent signal.

The emitted fluorescent light from the source region (17) is transmitted to the collection optical elements (19) along the collection path (18). The collection path (18) can extend through the optical element (16) in the base (11) of the sample well, as shown in FIG. 7. In an alternative embodiment, the collection path can extend through the well in the sample array to a location on the opposite side of the sample array, as shown in FIG. 1, for example. In both embodiments, the collection optical elements (19) are configured to collect and focus the light emitted from the source region, as was described above.

There are several ways to configure the collection optical elements (19) that allow the scanning of a large array, such as a microarray plate. One geometry is shown in FIGS. 4, 5A and 5B. In this embodiment, the collection optical elements (19) is a rod lens, which is designed to capture the entire range of the sweep of the beam (10) over one dimension of the base of the sample array. The collection optical elements (19) can include other types of lenses or lens combinations, as would be determined by the specific information required from the fluorescent emission. As a result of light collimation by a single collection lens (19) as shown in FIGS. 4, 5A and 5B, all light emitted from a position on the array cell or microarray plate can be imaged, and collected with high efficiency.

Figure 8:
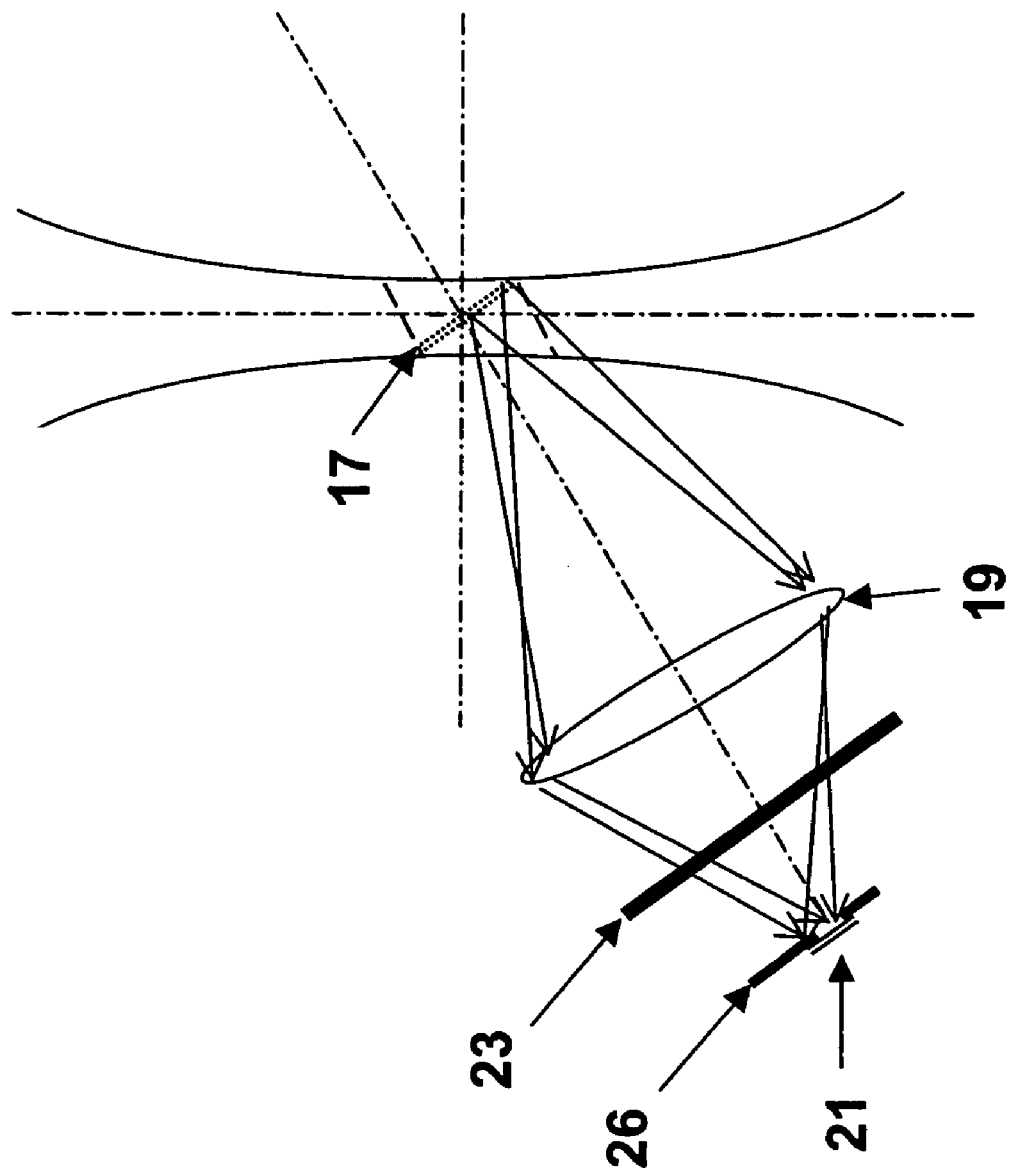
FIG. 8 is a schematic diagram showing a more detailed view of the confined field of view for a single detector configuration of FIG. 7.

As can be seen in FIG. 8, another embodiment of the collection optical elements (19) includes an optical transmission filter (23) and a slit aperture (26). Before passing the fluorescent light collected by the rod lens (19) to the detector (21), the light is appropriately filtered by the transmission filter (23), which is designed to pass the fluorescence emission. Alternatively, several filters can be chosen to minimize the amount of laser light to be detected by the detector (21). The optical filter (23) is chosen to optimize the collection of information within the spectral region of light emitted by the source region (17). For example, in one embodiment, the laser light is between 400 and 500 nm in wavelength, and the emitted fluorescence is in the region above 500 nm, and the optical filter (23) is a 500 nm long pass filter located behind the rod lens (19). Many other configurations can be envisioned by people skilled in the art, depending on the wavelengths of the incident and the emitted light, and the filters chosen.

The slit aperture's (26) opening is located directly in front of the entrance to the detector (21) or optical fiber (20) coupled to the detector (20). As can be seen in FIG. 8, the light that is emitted from the center of the source region (17) is collected by the rod lens (19) and passes through the center of the slit aperture (26). On the other hand, light that is emitted from regions at a different depth of the sample, such as from the edge of the source region (17) will be imaged by the rod lens (19) outside the slit aperture's (26) opening, and will thus not be collected. The advantage of further confining the focal region is that an improved spatial resolution will result, as well as further discrimination of background fluorescence outside of the region. In one embodiment, an aperture size of 250 microns results in approximately a 400 micron detection region. As the skilled reader will realize, combinations are also possible in which there is only an optical transmission filter (23) or slit aperture (26), but not both.

Figure 9:
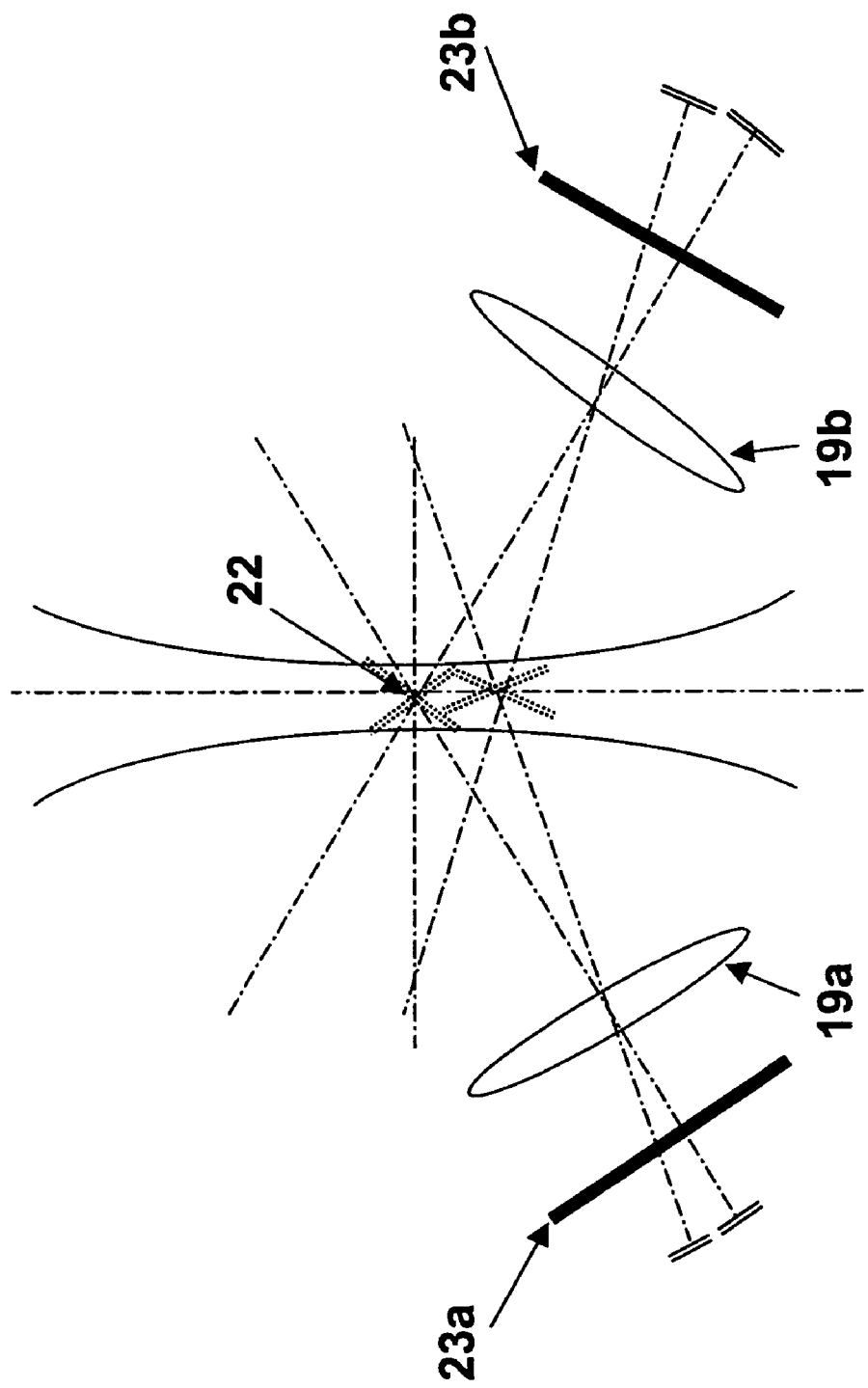
FIG. 9 is a schematic diagram showing a confined field of view in a stereo configuration of the apparatus of FIG. 1 with multiple detectors.
Figure 10:
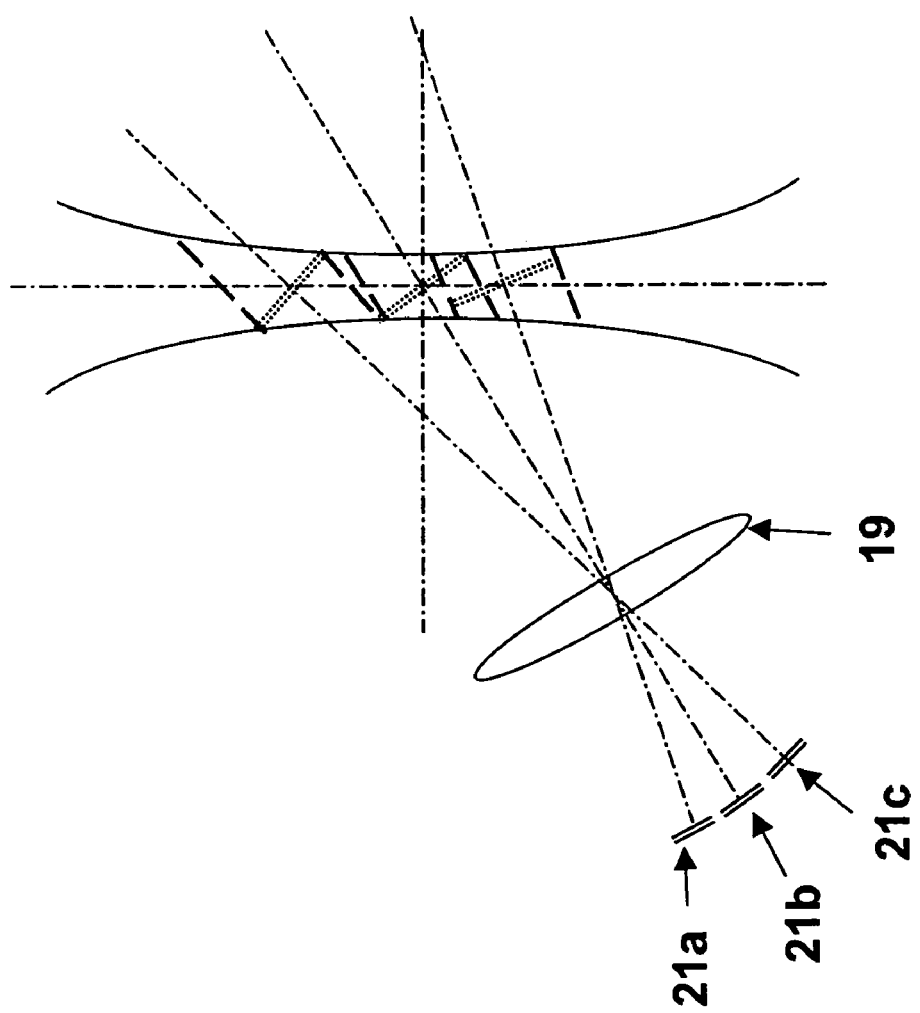
FIG. 10 is a schematic diagram showing multiple confined fields of view for an array of detectors of the apparatus of FIG. 1.

In another embodiment, which is shown in FIG. 9, two or more collection optics arrangements (19a, 19b) are provided. With a stereo configuration of the collection lenses (19a, 19b) as shown in FIG. 9, the focal field for the two lenses can have improved confinement over the single field generated by one lens and the focusing source shown and discussed above with respect to FIG. 8. The improvement is schematically represented in FIG. 9 by the intersection (22) of the focal planes for the respective collection optics arrangements (19a, 19b), corresponding to the main object planes of the lenses (19a, 19b).

The setup of FIG. 9 with two sets of collection optics (19a, 19b) can also be used for simultaneous collection of orthogonal components of emission from a polarized excitation source. A first polarizing filter (23a) can be used to pass only light of a first polarization to a first detector (21a), and a second polarizing filter (23b) can be used to pass only light of a second, orthogonal, polarization to a second detector (21b). The correlation of the signals collected in this configuration, detection in the detection system, and subsequent manipulation of the stored signal give rise to information not available to a single detector, with attendant improvement in signal. The information derived from this apparatus is steady-state anisotropy. Furthermore, with lifetime capability one can measure the correlation of time dependent behavior of fluorescence anisotropy. Time-resolved anisotropy of the emissions signal can give dynamical and/or structural information on biomolecules and their environment. It is important that any polarization filtering is performed before the collected light enters any optical fibers, since the optical fibers distort the polarization information and light that is output from an optical fiber does not have identical polarization components to the light that was input to the optical fiber at the other end.

As was discussed above, the detector (21) can be a detector with high gain, such as a photomultiplier tube (PMT). Other examples of detectors are photodiodes, various types of charge coupled devices (CCDs), or microchannel plates. The detector (21) does not have to be physically located adjacent to the collection optical elements (19), but the light can be transmitted from the collection optical elements (19) to the detector (21) through a fiber array (20). In one embodiment, shown in FIG. 10, multiple detectors (21a-21c) are arranged adjacent to each other in order to collect the signal from the collection optical elements (19). In this case, the individual detectors (21a-21c) each have their own confined field of view, with the attendant advantages associated with the confined focal region as described above for one detector. Just like with a single detector, the multiple detectors (21a-21c) do not have to be physically located adjacent to the collection optical elements (19), but the light can be transmitted from the collection optical elements (19) to each of the detectors (21a-21c) through a fiber array (20), or relay lens system for each detector. This multi-detector arrangement has additional advantages, such as the ability to simultaneously detect signal at multiple locations, such as at different depths, within the source region (17) and to assign these signals to spatial locations within the sample (2). Alternatively, the multiple detectors (21a-21c) can be configured with optical filters (not shown in FIG. 10), and used to collect fluorescent emission from different spectral regions. In yet another embodiment, the multiple detectors (21a-21c) can be configured to detect orthogonal polarization signals, as described above, allowing for simultaneous detection of the anisotropy of the fluorescent signal.

Figure 11:
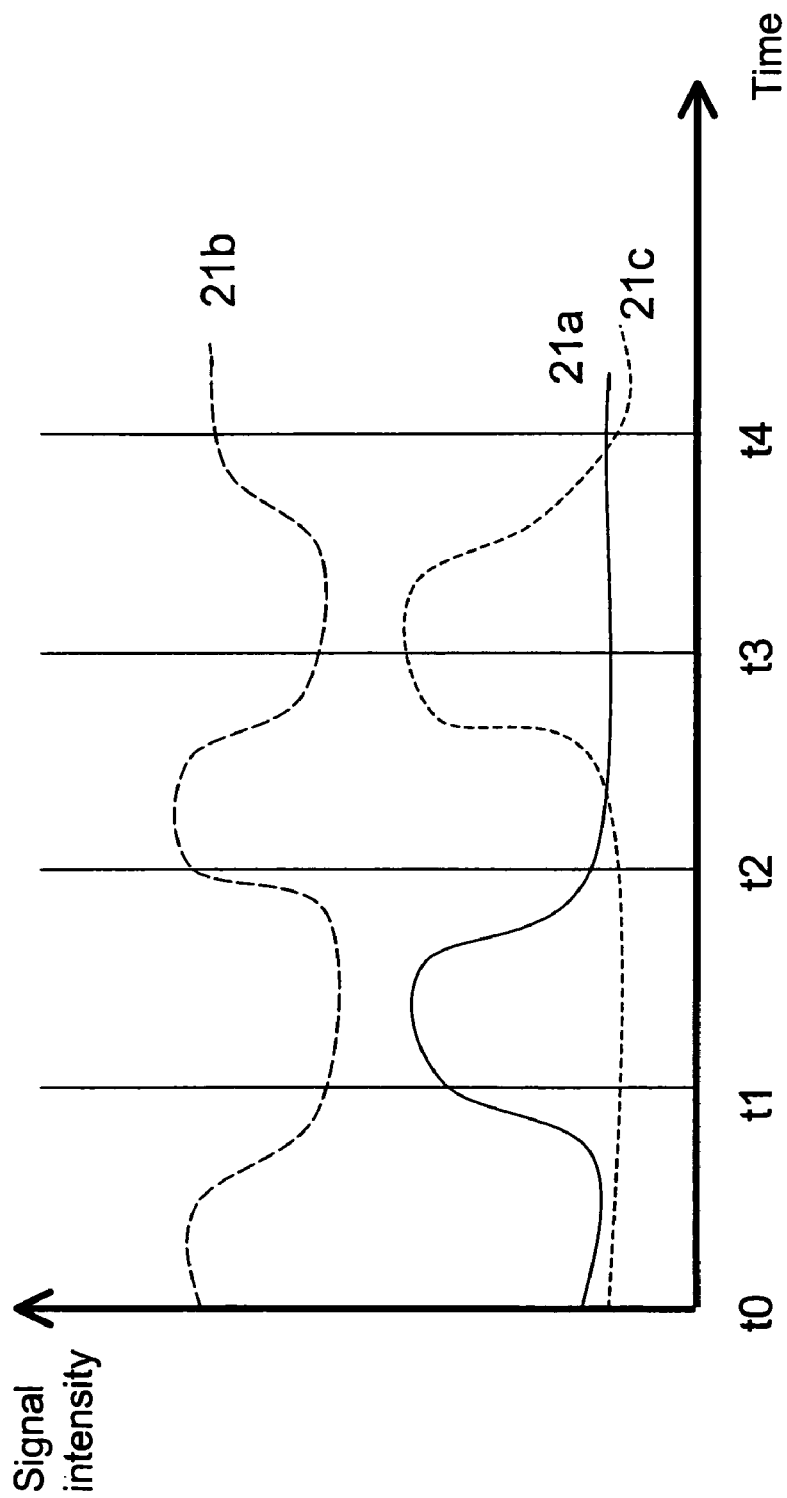
FIG. 11 is a schematic diagram showing output signals as a function of time from three individual detectors in a multi-detector configuration of the apparatus of FIG. 1.

The detectors (21a-21c) can also be used to correct the sample position based on the recorded signals, as can be seen in FIG. 11. Assume, for example, that it is desired to keep the sample (2) aligned with the collection optics, so that most of the signal is received by the middle detector (21b). Since each detector (21a-21c) is associated with a different depth, it can be expected that the middle detector (21b) should have a signal that is higher than the outer detectors (21a, 21c). As can be seen in FIG. 11, at time t0, only the middle detector (21b) registers a signal, whereas the outer detectors (21a, 21c) are not picking up any signals. At time t1, the sample's (2) physical position has shifted, such that only one of the outer detectors (21a) picks up a signal. This indicates that the sample (2) position must be adjusted, so the apparatus moves the sample (2) until only the middle detector (21b) picks up a signal, as can be seen at time t2. At time t3, the sample (2) has moved again, but in this case in the other direction, such that only the other outer detector (21c) picks up a signal. This indicates that the sample (2) position must be adjusted in the other direction, and consequently the apparatus moves the sample (2) until only the middle detector (21b) again picks up the signal, which can be seen at time t4. This technique can be used to move the sample (2) not only in the vertical direction, but also in the horizontal direction, depending on the detector arrangement. If multiple detector arrangements are used, such as in three orthogonal directions, complete control over the sample positioning can be achieved in all spatial directions. Since movement within a horizontal plane can occur with two degrees of freedom, it is necessary to have two sets of detectors that preferably are oriented perpendicular to each other within the horizontal plane. With this detector arrangement, a horizontal translation of the sample will result in an increased signal in one or both detector sets, and the movement can be unambiguously identified.

As can be seen in FIG. 1, the apparatus also contains logic, such as a data acquisition system (14), a data processing and storage system (24), and a controller (15), which work in conjunction with the above-described optical and mechanical components of the apparatus to provide adequate control capabilities for the various types of investigations that can be carried out with the apparatus. The signal from the detector (21) is enhanced by the data acquisition system (14), and then stored into the data processing and storage system (24). The data processing and storage system (24) contains a fast A/D converter, or accepts digital information from the data acquisition system (14) directly. The data processing and storage system (24) can, for example, be a digitizing storage oscilloscope, or a computer with instructions encoded in software for collecting and storing the detected or enhanced emission signal.

The signal can be labeled using a triggering event in time, and can be co-located with a spatial position of the fluorescing object within a well of a microarray, or with the macro location of the well in the microarray plate. The software logic in the data processing and storage system (24) can contain instructions for deriving one or more object characteristics from the emission signal, such as total intensity, average intensity, peak intensity, size, Gaussian or other waveform fit, or other such characteristics as may be found useful to those skilled in the art. The trigger signal can be modified by the controller (15) as needed to configure a delay, a blanking signal, a duty cycle, or provide a means by which the trigger circuit of a boxcar averager, for example, can be activated. Two triggering events at the start and end of a scan can be used to measure the total scan time and correct for scan jitter. This also enables bidirectional scanning. There are many permutations for using this data processing and data storage system (24) that are not described here, but which are useful to those skilled in the art.

In the interest of efficient data storage, due to the large size of multi-channel images, the data processing and storage system (24) can be set up such that data is only collected and saved when a relevant part of the sample (2), such as a cell, is illuminated. In one embodiment, this is accomplished by setting a threshold value in the data processing and storage system (24), and saving data only when the intensity of the collected fluorescent light exceeds the threshold value for a certain period of time, or whenever some other pre-determined criterion is satisfied. In another embodiment, the data processing and storage system (24) only saves data during certain time intervals, such as when the illuminating beam (10) illuminates a well or a location in a microarray. Thus, instead of using intensity values to determine when to save data, the data is saved based on the positions of the light beam (10) at any given time, as determined by the scanner (5) and the multi-element lens (9).

In one embodiment, the apparatus allows for measurement of successive laser pulses, as a result of modulating the laser light, over the same spatial location of the scan region and then subsequently analyzing the fluorescent signal measured by the detector (21) to determine a time-dependent response of the sample within the scanned region. The response can include one or more characteristics of the sample, such as molecular interactions, protein-protein interaction, binding kinetics, drug/target interactions, cell apoptosis, and so on. The timing and response to time dependent perturbations, such as the excitation pulse, form important aspects of this invention. The timing associated with the emission event with respect to the incident laser pulse, such as a signal timing or an emission lifetime, is captured by the configuration as described above. The detection of native or engineered materials will give rise to information concerning chemical or biological activity, as will be apparent to those skilled in the art, and the detection of induced or engineered fluorescence will also give rise to such information as has been described above.

In another embodiment, the detector (21) can be arranged to collect information stored in the incident light as well as the emitted light, such as the polarization of the light. In this embodiment, the light source (1) is polarized, the incident polarization is determined, and the fluorescent response emitted by the sample (2) is analyzed for its polarization components, or anisotropy. The polarization of the incident light and/or the fluorescent light can be modulated, for example, by the electrooptic device (8). The timing of the modulation of the polarized signals is controlled by the controller (15) with respect to the timing of the scans, so that quick, successive scans with orthogonal polarization can be performed and so that dynamical information from the fluorescent polarization can be extracted. Furthermore, the intensity of the incident light can be modulated to collect time-dependent information from the sample. The detection of fluorescent polarization and the time-dependence in materials gives rise to information concerning physical, chemical or biological activity, as will be apparent to those skilled in the art, and the detection of induced or engineered fluorescence polarization will also give rise to such information as for example the result of a fluorescence polarization immunoassay, or other that has been described above.

Figure 6:
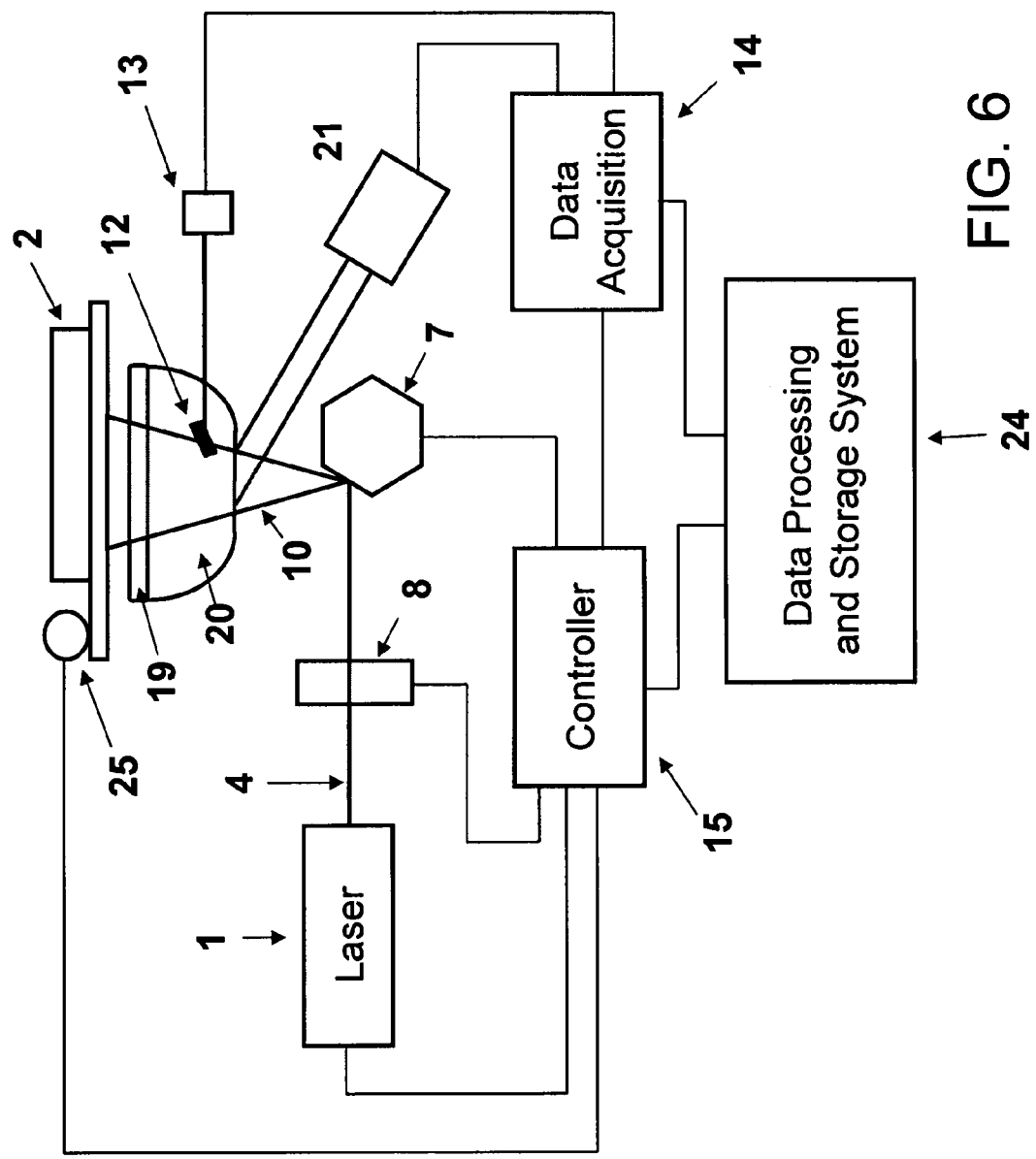
FIG. 6 is a more detailed schematic view of the detection optics and electronics system of an apparatus for collecting optical data in accordance with the invention.

In one embodiment, as shown in FIG. 6, the sample (2) can be placed on a moveable platform (25) that can be used to position the sample (2). For example, the platform can handle a microarray plate containing 96-sample wells, or a 3456-well plate for addressing very large arrays of tests and samples. A raster scan, or focused line of light (10) is provided to the sample (2) and the emission is collected by the collection optical elements (19) in such a way the arrays can be addressed in a parallel fashion. The parallel addressable nature of the invention allows for very high throughput scanning and data collection, which is useful for example, for interrogating and screening therapeutic effects of chemicals on biomaterials as described above.

The platform (25) can be configured to move with a precision that is either less than or on the order of the optical resolution of the multi-element lens (9), such that the motion of the platform (25) gives rise to high-resolution images of the sample (2). For example, the scanned beam (10) is swept across the sample (2) in one dimension and the sample array is moved in a perpendicular direction to the sweep by the platform (25), whereby the movement is timed such that the beam makes one or more complete excursions, and the emission signal from the detector (21) derived from one or more complete sweeps is collected and summed or manipulated by the data acquisition system (14) and the data processing and storage system (24). In this embodiment, the platform (25) motion is perpendicular to the motion of the scan (10), such that a two-dimensional image of the sample (2) can be reconstructed using the instructions encoded in the data processing and storage system (24).

In another embodiment, the focus location of the multi-element lens (9) in the source region (17) can provide spatial information in the direction perpendicular to the plane defined by the scan (10) and platform (25) motion, resulting in a reconstructed 3-dimensional image.

In another embodiment, the time domain information reconstructed by the data acquisition system (14) and the data processing and storage system (24) can be used to construct image spatial locations, which can give rise to information on the objects in sample array, such as events that occur as a result of the light probe. Alternatively, the information may result from, for example, non-light-induced drug or responses at the cellular or subcellular level.

A number of embodiments of the invention have been described. Nevertheless, it will be understood that various modifications may be made without departing from the spirit and scope of the invention. For example, the apparatus may perform the scanning function by moving the sample (2) only, instead of using a scanning device (5) to move the beam (4) from the light source (1) across the sample. The invention has been described above with regards to fluorescent light, but the same principles can be applied to the collection of phosphorescent light, which may be useful for investigations of certain samples. The invention can also be used to perform measurements of chemiluminescence and resonant energy transfers. Accordingly, other embodiments are within the scope of the following claims.

The invention claimed is:

1. An apparatus for collecting optical data pertaining to one or more characteristics of a sample, the apparatus comprising:
   a light source;
   one or more illumination optical elements configured to direct a light beam from the light source and to focus onto the sample close to the light beam's diffraction limit, the one or more illumination optical elements comprising a scanner configured to move the light beam relative to at least one illumination optical element and to scan close to the diffraction limit across the sample in a straight line;
   one or more collection optical elements configured to collect light from the sample across a scan of the light beam and to transmit the collected light from across the scan to two or more detectors offset from one another with respect to a path configured to collect the light from the sample and configured to output a single non-spatially resolved signal without the collection light being incident to the one or more illumination optical elements, wherein none of the one or more collection optical elements are included among the one or more illumination optical elements, wherein each of the two or more detectors is positioned to capture light being emitted from a different vertical depth within the sample; and a device forming an aperture that limits detection of light from the sample to light associated with a limited vertical depth within the sample, wherein the device is one of the collection optical elements.

2. The apparatus of claim 1, wherein the device forming the aperture is a slit aperture.

3. The apparatus of claim 1, wherein the device forming the aperture is a bundle of optical fibers.

4. The apparatus of claim 3, wherein light entering different optical fibers in the bundle of optical fibers corresponds to light at different vertical depths within the sample.

5. The apparatus of claim 1, wherein the collection optical elements collect light from a scan line on the sample with substantially uniform efficiency.

6. The apparatus of claim 5, wherein the collection optical elements include one of a cylindrical lens and a spherical lens.

7. The apparatus of claim 1, further comprising logic for controlling an adjustable sample holder with respect to the collection optical elements in response to light intensity detected at the two or more detectors to maintain a consistent vertical position of the sample with respect to the collection optical elements during scanning.

8. The apparatus of claim 1, wherein the two or more detectors include at least one of: a photomultiplier detector, a photodiode device, a charge coupled device, and a microchannel plate.

9. The apparatus of claim 1, wherein the two or more detectors are configured to receive light from the same region of the sample and to detect two or more different characteristics of the sample.

10. The apparatus of claim 9, wherein the two or more different characteristics include different polarizations of the light, different frequencies of the light, and different lifetimes.

11. The apparatus of claim 9, further comprising logic for examining the correlation between the signals obtained from the two or more detectors to identify objects and exclude background noise.

12. The apparatus of claim 1, further comprising logic for limiting collection of optical data to regions of the sample known or detected to hold particular objects to be characterized on the sample, the logic being implemented in computer software or computer hardware instructions that can be read and executed by a process operatively connected to the two or more detectors.

13. The apparatus of claim 12, wherein the logic for limiting collection of optical data limits collection by only recording optical data when an intensity of the collected light is above a certain adjustable threshold value.

14. The apparatus of claim 12, wherein the logic for limiting collection of optical data limits collection by only recording optical data during time periods when the beam from the light source is scanned across an area of interest on the sample.

15. The apparatus of claim 1, wherein the light source is one of: a continuous wave laser, a pulsed laser, a mode-locked high repetition rate laser, and a Q-switched laser.

16. The apparatus of claim 15, wherein the continuous wave laser is selected from the group consisting of a diode laser, a diode-pumped solid state laser, a gas laser, and a tunable solid state laser system.

17. The apparatus of claim 15, wherein the continuous wave laser is modulated in a frequency range of 1 kilohertz to 2 Gigahertz.

18. The apparatus of claim 15, wherein the pulsed laser is configured to emit pulses in a frequency range of 1 Hertz-100 Megahertz with a spacing ranging from 10 nanoseconds to 1 second.

19. The apparatus of claim 15, wherein the mode-locked laser has a repetition rate that is higher than or equal to 10 Megahertz.

20. The apparatus of claim 15, wherein the Q-switched laser is pulsed at a frequency in a range of 1 Hertz to 1 Megahertz.

21. The apparatus of claim 1, wherein the light beam emitted from the light source is intensity modulated in time with a frequency in a range of 1 Hertz to 2 Gigahertz.

22. The apparatus of claim 1, wherein the scanner includes one or more polygonal mirrors being rotated by a scanning element to scan the light beam across the sample.

23. The apparatus of claim 1, wherein the scanner includes one or more mirrors being moved by a galvanometer to scan the light beam across the sample.

24. The apparatus of claim 1, wherein the scanner is a resonant mirror scanner.

25. The apparatus of claim 1, wherein the one or more illumination optical elements include a telecentric lens.

26. The apparatus of claim 1, further comprising a row of optical transmission elements for transmitting the collected light from across the scan to the two or more detectors.

27. The apparatus of claim 1, wherein the apparatus is configured so that a distribution of the collected light across the scan is determined by synchronizing an excitation scan time with a collection time.

28. The apparatus of claim 1, wherein the scanner comprises a scanning element configured to interact with the light beam and to direct it to scan in said straight line across the sample, and wherein the collected light from the sample does not interact with the scanning element.

29. The apparatus of claim 28, wherein the scanning element is disposed between the light source and a scanning lens.

30. The apparatus of claim 29, wherein the scanning element is configured to scan over a distance of at least 5 millimeters on the sample.

31. An apparatus for collecting optical data pertaining to one or more characteristics of a sample, the apparatus comprising:
    a light source;
    one or more illumination optical elements configured to direct a light beam from the light source of a first frequency onto the sample and to focus the light beam onto the sample close to the light beam's diffraction limit, the one or more illumination optical elements comprising a scanner configured to move the light beam relative to at least one illumination optical element and to scan close to the diffraction limit across the sample in a straight line over a distance of at least 5 millimeters; and
    one or more collection optical elements configured to collect light of a second frequency from the sample across a scan of the light beam and to transmit the collected light from across the scan to two or more detectors offset from one another with respect to a path configured to collect the light from the sample and configured to output a single non-spatially resolved signal without the collection light being incident to the one or more illumination optical elements, wherein none of the one or more collection optical elements are included among the one or more illumination optical elements, wherein each of the two or more detectors is positioned to capture light being emitted from a different vertical depth within the sample, and wherein the first and second frequencies are different.

32. The apparatus of claim 31, wherein the collection optical elements include a bandpass filter and/or a cutoff filter for determining the second frequency.

33. The apparatus of claim 31, further comprising logic for controlling an adjustable sample holder with respect to the collection optical elements in response to light intensity detected at the two or more detectors to maintain a consistent vertical position of the sample with respect to the collection optical elements during scanning 34. The apparatus of claim 31, wherein the two or more detectors are configured to receive light from the same region of sample and to detect two or more different characteristics of the sample.

35. The apparatus of claim 34, wherein the two or more different characteristics include different polarizations of the light, different frequencies of the light, and different lifetimes.

36. The apparatus of claim 31, further comprising logic for limiting collection of optical data to regions of the sample known or detected to hold particular objects to be characterized on the sample, the logic being implemented in computer software or computer hardware instructions that can be read and executed by a processor operatively connected to the detector.

37. The apparatus of claim 36, wherein the logic for limiting collection of optical data limits collection by only recording optical data when an intensity of the collected light is above a certain adjustable threshold value and the optical data meets at least one additional criterion.

38. The apparatus of claim 36, wherein the logic for limiting collection of optical data limits collection by only recording optical data during time periods when the beam from the light source is scanned across an area of interest on the sample.

39. The apparatus of claim 31, wherein the one or more collection optical elements include a device forming an aperture that limits detection of light from the sample to light associated with a limited depth of focus within the sample.

40. The apparatus of claim 39, wherein the device forming the aperture is a slit aperture.

41. The apparatus of claim 39, wherein the device forming the aperture is a bundle of optical fibers.

42. The apparatus of claim 41, wherein light entering different optical fibers in the bundle of fibers corresponds to light at different vertical depths within the sample.

43. The apparatus of claim 31, wherein the one or more illumination optical elements include a telecentric lens.

44. The apparatus of claim 31, further comprising a row of optical transmission elements for transmitting the collected light from across the scan to the two or more detectors.

45. The apparatus of claim 31, wherein the apparatus is configured so that a distribution of the collected light across the scan is determined by synchronizing an excitation scan time with a collection time.

46. The apparatus of claim 31, wherein the scanner comprises a scanning element configured to interact with the light beam and to direct it to scan in said straight line across the sample, and wherein the collected light from the sample does not interact with the scanning element.

47. The apparatus of claim 46, wherein the scanning element is disposed between the light source and a scanning lens.

48. The apparatus of claim 47, wherein the scanning element is configured to scan over a distance of at least 5 millimeters on the sample.

49. An apparatus for collecting optical data pertaining to one or more characteristics of a sample, the apparatus comprising:
a light source;
one or more illumination optical elements configured to direct a light beam from the light source and to focus onto the sample close to the light beam's diffraction limit, the one or more illumination optical elements comprising a scanner configured to move the light beam relative to at least one illumination optical element and to scan close to the diffraction limit across the sample in a straight line;
one or more collection optical elements configured to collect light from the sample across a scan of the light beam and to transmit the collected light from across the scan to one or more detectors, each configured to output a single non-spatially resolved signal without the collection light being incident to the one or more illumination optical elements;
a first device that limits detection of light from the sample to light associated with a first vertical depth within the sample, and
a second device that limits detection of light from the sample to light associated with a second, different, vertical depth within the sample,
wherein the first and second devices are collection optical elements.

50. The apparatus of claim 49, further comprising logic for controlling a vertically adjustable sample holder with respect to the collection optical elements in response to the relative light intensity collected at the first and second devices in order to maintain a consistent vertical position of the sample with respect to the collection optical elements during scanning 51. The apparatus of claim 49, wherein at least one of the first device and the second device is an optical fiber.

52. The apparatus of claim 51, wherein the first device comprises a first row of optical fibers and the second device comprises a second row of optical fibers.

53. The apparatus of claim 49, wherein the one or more detectors comprise one or more microchannel plates arranged to separately detect light from the first and second devices.

54. The apparatus of claim 49, wherein the one or more detectors includes at least one of: a photomultiplier detector, a photodiode device, a microchannel plate, and a charge coupled device.

55. The apparatus of claim 49, further comprising two or more detectors configured to receive light from the sample and to detect two or more different characteristics of the light from the sample.

56. The apparatus of claim 49, wherein the light beam from the light source is monochromatic having a first wavelength and wherein one or more of the collection optics and the one or more detectors is tuned to collect light at a second wavelength, which is different from the first wavelength.

57. The apparatus of claim 41, further comprising a third device that limits detection of light from the sample to light associated with a third, different, vertical depth within the sample.

58. The apparatus of claim 49, further comprising a row of optical transmission elements configure to transmit the collected light from across the scan to the two or more detectors.

59. The apparatus of claim 49, wherein the apparatus is configured so that a distribution of the collected light across the scan is determined by synchronizing an excitation scan time with a collection time.

60. The apparatus of claim 49, wherein the scanner comprises a scanning element configured to interact with the light beam and to direct it to scan in said straight line across the sample, and wherein the collected light from the sample does not interact with the scanning element.

61. The apparatus of claim 60, wherein the scanning element is disposed between the light source and a scanning lens.

62. The apparatus of claim 61, wherein the scanning element is designed to scan over a distance of at least 5 millimeters on the sample.

* * * * *